United States Patent [19]

Wakumoto et al.

[11] Patent Number: 5,122,061
[45] Date of Patent: Jun. 16, 1992

[54] CURABLE ADHESIVE COMPOSITIONS

[75] Inventors: Sadao Wakumoto; Kazuo Ito, both of Tokyo; Takeshi Sakashita, Yamaguchi, all of Japan

[73] Assignee: Mitsui Petrochemical Industries, Ltd., Tokyo, Japan

[21] Appl. No.: 166,020

[22] Filed: Mar. 9, 1988

[30] Foreign Application Priority Data

Mar. 9, 1987 [JP] Japan .................. 62-52160

[51] Int. Cl.$^5$ .................. A61C 13/23; A61K 6/68; A61K 5/01
[52] U.S. Cl. .................. 433/228.1; 433/226
[58] Field of Search ............... 433/226, 228.1, 201.1

[56] References Cited

FOREIGN PATENT DOCUMENTS

| 0051796 | 5/1982 | European Pat. Off. |
| 2321215 | 11/1973 | Fed. Rep. of Germany |
| 2739282 | 3/1978 | Fed. Rep. of Germany |
| 53-39331 | 4/1978 | Japan |
| 60-44508 | 3/1985 | Japan |
| 2000789 | 1/1979 | United Kingdom |

OTHER PUBLICATIONS

Hitomi Shimizu et al., "Adhesion of 4-META/M-MA-TBB Resin to Bovine Tooth Substrates Treated with EDTA", Japanese Dental and Hygienic Journal, vol. 28. 270 (1985) (partial translation).

*Primary Examiner*—V. Millin
*Attorney, Agent, or Firm*—Sherman and Shalloway

[57] ABSTRACT

A two part curable adhesive composition for use as adhesive for dental composite resin is provided, as a first part (i) a solution comprising a radical polymerizable acrylate or methacrylate monomer having in its molecule at least one group selected from the group consisting of hydroxyalkyl, hydroxyalkylene, amide, oxyalkylene and polyoxyalkylene groups, and a colvent for said radical polymerizable acrylate or methacrylate monomer; and as a second part (ii) a curable composition comprising (P) a monofunctional acrylate or methacrylate monomer, (Q) a polyfunctional acrylate or methacrylate monomer, (R) an acrylate or methacrylate monomer containing an acidic group and at least one acryloyloxyl or methacryloyloxyl group in its molecule, and (S) a trialkylboron or an oxide thereof; wherein said component (S) is maintained separate from said components (P), (Q) and (R) until immediately before use. A method for applying the above-described two-part curable adhesive composition to a dental area is provided, comprising: dissolving said radical polymerizable acrylate or methacrylate monomer in said solvent to form said solution (i); applying said solution (i) to a dental area; removing said solvent from said applied solution to form a coated area; mixing said components (P), (Q) and (R) with said component (S) to form said composition (ii); applying said composition (ii) to said coated area immediately after mixing to form a coating, and curing said coating.

3 Claims, No Drawings

CURABLE ADHESIVE COMPOSITIONS

BACKGROUND OF THE INVENTION

This invention relates to curable adhesive compositions for dental use.

A number of adhesive compositions have been proposed for orthodontic and restorative treatments. Typical are catalyzed compositions comprising a radical polymerizable monomer such as an acrylate or methacrylate vinyl monomer. For example, Japanese Patent Application Kokai No. 60-44508 proposes a curable composition comprising an acrylate or methacrylate vinyl monomer, an aromatic carboxylic acid or anhydride containing an acryloyloxyl or methacryloyloxyl group, an amine, and a sulfinic acid or a salt thereof. Japanese Patent Application Kokai No. 53-39331 discloses an adhesive composition comprising an acrylate or methacrylate ester which is liquid at room temperature, an amine, a sulfinic acid or a salt thereof, and a peroxide. Nihon Shika Hoken (Japanese Dental and Hygienic Journal), 28, 270 (1985) reports an adhesive composition comprising methyl methacrylate, 4-META, and a partial oxide of tributylboran (TBB-O). However, most conventional adhesives and curable compositions fail to sufficiently bond and fit to tooth substance, particularly, dentin treated with a mild etching agent such as ethylenediaminetetraacetic acid (EDTA) and non-etched dentin.

SUMMARY OF THE INVENTION

An object of the present invention is to provide a curable composition having improved curability at room temperature and water-resistant adherence.

Another object of the present invention is to provide a curable composition having improved adherence and fitness to enamel and dentin, particularly the latter.

A further object of the present invention is to provide a curable composition which can be used as a dental adhesive to bond composite resins for tooth restoration without any adverse influence including stimulation of dental pulp.

A further object of the present invention is to provide a method for applying to a dental area, a two-part curable adhesive composition having improved adherence and fitness to enamel, dentin and bond composite resins.

According to the present invention, there is provided a curable adhesive composition comprising in combination, (i) a solution containing a radical polymerizable acrylate or methacrylate monomer having in its molecule at least one group selected from the class consisting of hydroxyalkyl, hydroxyalkylene, amide, oxyalkylene, and polyoxyalkylene groups, and (ii) a curable composition comprising (P) a monofunctional acrylate or methacrylate monomer, (Q) a polyfunctional acrylate or methacrylate monomer, (R) an acrylate or methacrylate monomer containing an acidic group and at least one acryloyloxyl or methacryloyloxyl group in its molecule, and (S) a trialkylboron or an oxide thereof.

DETAILED DESCRIPTION OF THE INVENTION

Briefly stated, the curable adhesive composition of the present invention is based on a combination of (i) a solution containing a specific radical polymerizable acrylate or methacrylate monomer and (ii) a specific curable composition. It is to be noted that the term acrylate or methacrylate is sometimes described (meth)acrylate for brevity's sake.

The curable adhesive composition of the present invention contains (i) a solution of a radical polymerizable acrylate or methacrylate monomer. The monomer includes radical polymerizable acrylate or methacrylate monomers having in their molecule at least one group selected from a class consisting of hydroxyalkyl, hydroxyalkylene, amide, oxyalkylene, and polyoxyalkylene groups. These monomers are described in further detail.

Examples of the radical polymerizable acrylate or methacrylate monomer having a hydroxylalkyl group include 2-hydroxyethyl acrylate and methacrylate, 2-hydroxypropyl acrylate and methacrylate, and 2-hydroxybutyl acrylate and methacrylate. Preferred are 2-hydroxyethyl acrylate and methacrylate, and 2-hydroxypropyl acrylate and methacrylate.

Examples of the radical polymerizable acrylate or methacrylate monomer having a hydroxylalkylene group include monofunctional acrylate or methacrylate monomers of the general formula (I):

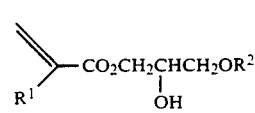

(I)

wherein
$R^1$ is H or $CH_3$,
$R^2$ is an aromatic residue such as

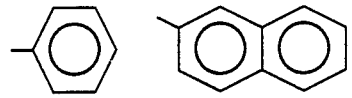

or an acyl residue such as

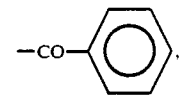

$-COCH_3$, and $-COC_7F_{15}$,
and epoxy acrylate or methacrylate monomers of the general formula (II):

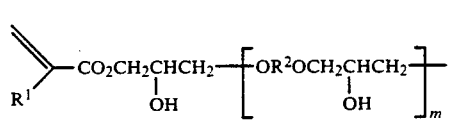

(II)

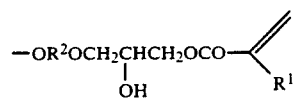

wherein
$R^1$ is H or $CH_3$,
$R^2$ is a hydrocarbon residue such as $-CH_2CH_2-$,

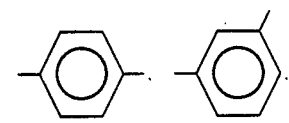

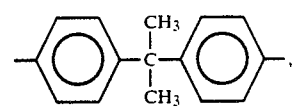

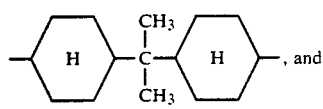, and m is 0 or a positive integer.

Some illustrative examples of the monofunctional acrylate or methacrylate monomer having formula (I) are shown below.

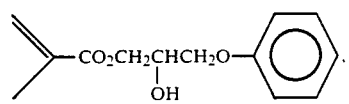

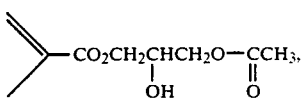

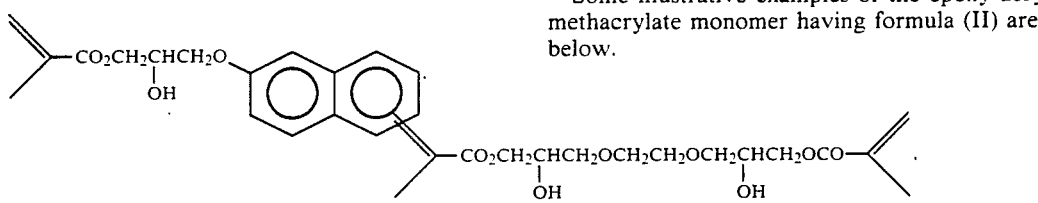

Among these monofunctional acrylate or methacrylate monomers, the following monomers are preferred.

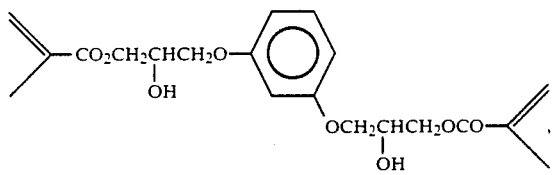

Some illustrative examples of the epoxy acrylate or methacrylate monomer having formula (II) are shown below.

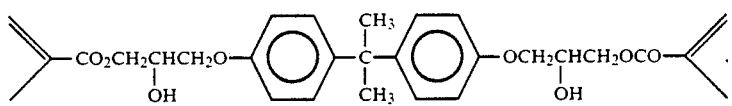

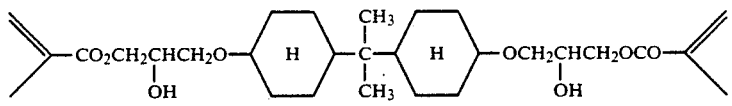

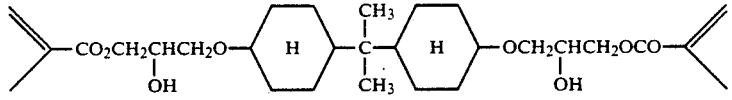

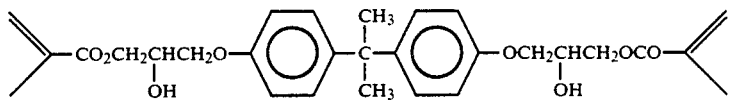

Among these monofunctional acrylate or methacrylate monomers, the following monomer is preferred.

The radical polymerizable acrylate or methacrylate monomers having an oxyalkylene or polyoxyalkylene group are acrylate or methacrylate monomers of the general formula (III):

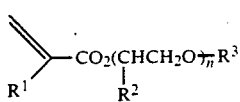
(III)

wherein
R$^1$ and R$^2$ each are H or CH$_3$,
R$^3$ is a hydrocarbon residue such as CH$_3$, C$_2$H$_5$, and

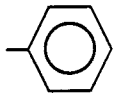

Some illustrative examples of the monomer of formula (III) are given below.

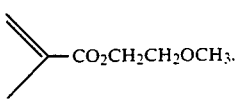

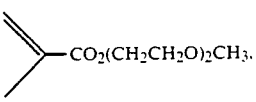

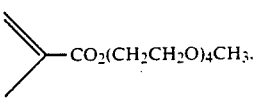

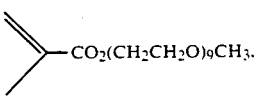

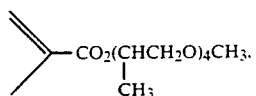

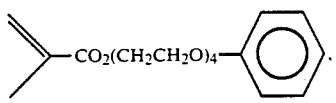

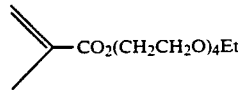

Among these acrylate or methacrylate monomers, the following monomers are preferred.

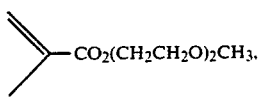

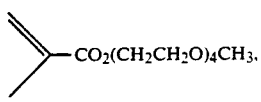

The radical polymerizable acrylate or methacrylate monomers having an amide group are amide-containing radical polymerizable acrylate or methacrylate monomers including acryl or methacrylamide monomers of the general formula (IV):

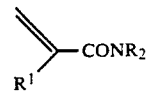
(IV)

wherein
R$^2$ is H or a hydrocarbon residue such as CH$_3$, C$_2$H$_5$, and

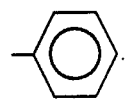

Some illustrative examples of the monomer having formula (IV) include

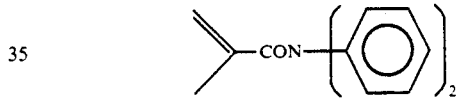

Among these amide-containing radical polymerizable acrylate or methacrylate monomers, the following monomer is preferred.

In the curable adhesive composition of the present invention, the radical polymerizable acrylate or methacrylate monomer is used in solution form. The solvents used to this end include water, acetone, and alcoholic solvents such as ethanol, propanol and butanol, as well as monofunctional acrylates or methacrylates having a relatively high rate of evaporation such as methyl acrylate and methacrylate, and ethyl acrylate and methacrylate. The solution generally contains the radical polymerizable acrylate or methacrylate monomer in such a solvent in a concentration of from 1 to 80% by weight, preferably from 2 to 50% by weight.

If desired, the solution of the radical polymerizable acrylate or methacrylate monomer may contain any desired additives, for example, an adhesion modifier such as glutaraldehyde, a polymerization retarder, and another radical polymerizable monomer.

The other constituent of the curable adhesive composition of the present invention is the curable composition (ii) comprising (P) a monofunctional acrylate or methacrylate monomer, (Q) a polyfunctional acrylate or methacrylate monomer, (R) an acrylate or methacrylate monomer containing an acidic group and at least one acryloyloxyl or methacryloyloxyl group in its molecule, and (S) a trialkylboron or an oxide thereof.

The monofunctional acrylate or methacrylate monomer (P) used in the curable composition (ii) may contain in its molecule a functional group other than an acidic group. Examples of the monofunctional acrylate or methacrylate monomer include acrylates and methacrylates containing a hydrocarbon group such as methyl acrylate and methacrylate, ethyl acrylate and methacrylate, butyl acrylate and methacrylate, hexyl acrylate and methacrylate, 2-ethylhexyl acrylate and methacrylate, dodecyl acrylate and methacrylate, lauryl acrylate and methacrylate, cyclohexyl acrylate and methacrylate, benzyl acrylate and methacrylate, and isobornyl acrylate and methacrylate; acrylates and methacrylates containing a hydroxyl group such as 2-hydroxyethyl acrylate and methacrylate, and 2-hydroxypropyl acrylate and methacrylate; acrylates and methacrylates containing an ethylene glycol unit such as ethylene glycol monomethyl ether acrylate and methacrylate, ethylene glycol monoethyl ether acrylate and methacrylate, ethylene glycol monododecyl ether acrylate and methacrylate, diethylene glycol monomethyl ether acrylate and methacrylate, polyethylene glycol monomethyl ether acrylate and methacrylate, and polyethylene glycol monoethyl ether acrylate and methacrylate; acrylates and methacrylates containing a fluorine-substituted group such as trifluoroethyl acrylate and methacrylate, and perfluorooctyl acrylate and methacrylate; silane acrylates and methacrylates such as γ-acryloyloxypropyltrimethoxysilane, γ-methacryloyloxypropyltrimethoxysilane, γ-acryloyloxypropyltri(trimethylsiloxy)silane, and γ-methacryloyloxypropyltri (trimethylsiloxy)silane; and tetrahydrofurfuryl acrylate and methacrylate. They may be used alone or in admixture of two or more.

Preferred are alkyl acrylates and methacrylates such as methyl acrylate and methacrylate, ethyl acrylate and methacrylate, hexyl acrylate and methacrylate, and dodecyl acrylate and methacrylate, and hydroxyl-containing acrylates and methacrylates such as 2-hydroxyethyl acrylate and methacrylate., and 2-hydroxypropyl acrylate and methacrylate. Most preferably, methyl methacrylate, n-hexyl methacrylate, 2-hydroxyethyl methacrylate and 2hydroxypropyl methacrylate monomers and a mixture thereof are used.

The polyfunctional acrylate or methacrylate monomer (Q) used in the curable composition (ii) of the curable adhesive composition according to the present invention is a polyfuncitonal acrylate or methacrylate monomer having at least two acryloyloxyl or methacryloyloxyl group in its molecule. Examples of the monomer (Q) include polyacrylates and polymethacrylates of alkane polyols such as ethylene glycol diacrylate and dimethacrylate, propylene glycol diacrylate and dimethacrylate, butylene glycol diacrylate and dimethacrylate, neopentyl glycol diacrylate and dimethacrylate, hexylene glycol diacrylate and dimethacrylate, and trimethylolpropane triacrylate and trimethacrylate; and polyacrylates and polymethacrylates of (poly)oxyalkane polyols such as diethylene glycol diacrylate and dimethacrylate, dipropylene glycol diacrylate and dimethacrylate, triethylene glycol diacrylate and dimethacrylate, tetraethylene glycol diacrylate and dimethacrylate, dibutylene glycol diacrylate and dimethacrylate, and dipentaerythritol hexaacrylate and hexamethacrylate; epoxy acrylates and methacryaltes of the general formula (V):

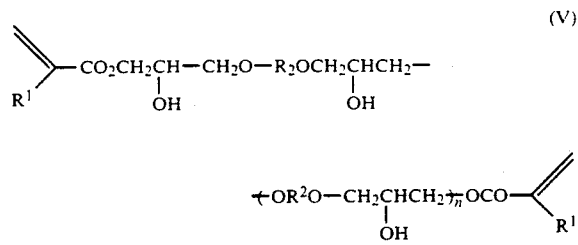

wherein
R$^1$ is H or CH$_3$,
n is 0 or a positive integer,
R$^2$ is —(CH$_2$)$_2$—, —(CH$_2$)$_4$—,

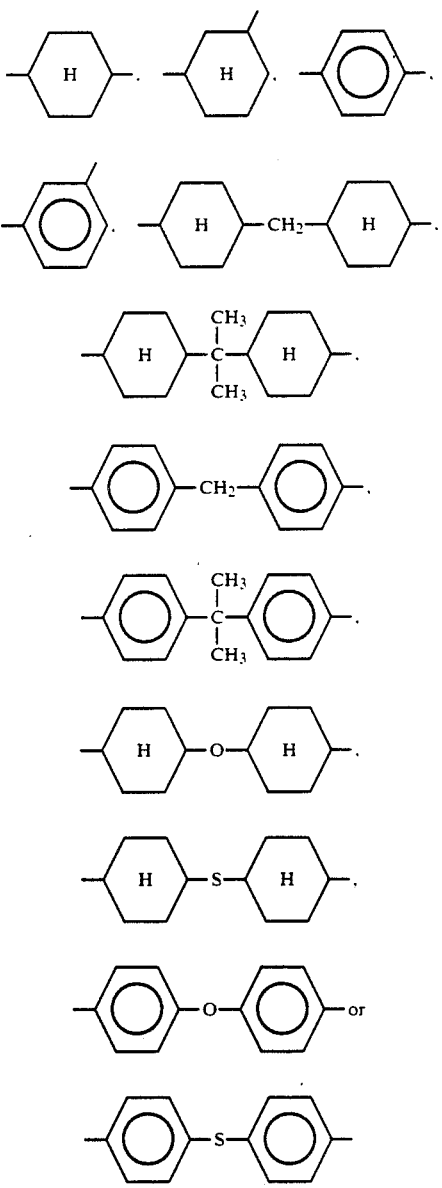

cycloaliphatic and aromatic diacrylates and dimethacrylates of the general formula (VI):

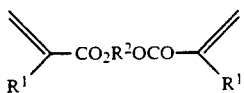 (VI)

wherein
R¹ is H or CH₃, and

R² is 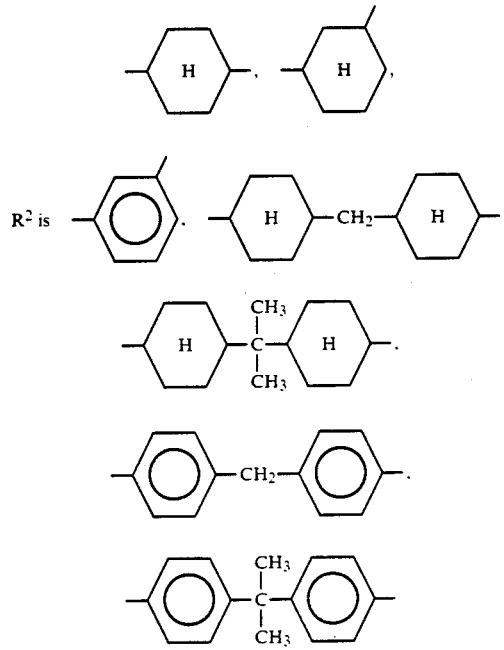

cycloaliphatic diacrylates and dimethacrylates of the general formula (VIII):

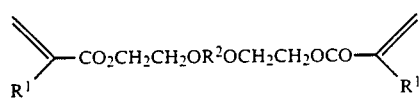 (VII)

wherein
R¹ is H or CH₃, and

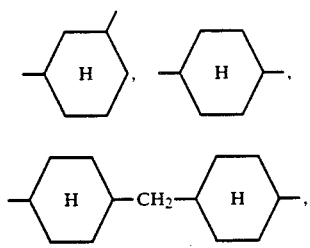

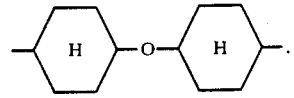

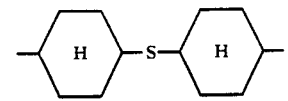

polyfunctional acrylates and methacrylates of the general formula (VIII):

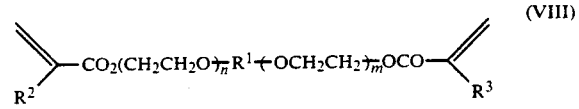 (VIII)

wherein R¹ is a divalent aromatic residue which has at least one aromatic ring and may have an oxygen or sulfur atom in its molecule,
R² and R³ each are hydrogen or a methyl group, and
n and m are positive integers,
examples of the divalent aromatic residue represented by R¹ in formula (VIII) including

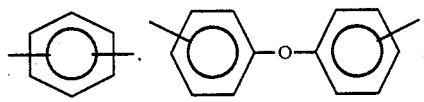

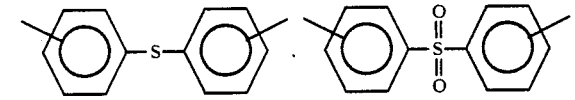

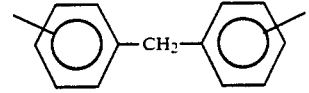

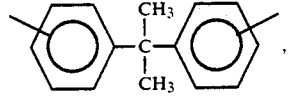

and polyfunctional acrylate and emthacrylate monomers having an urethane bond in their molecule such as

wherein R is H or CH₃,

wherein R is H or CH₃,

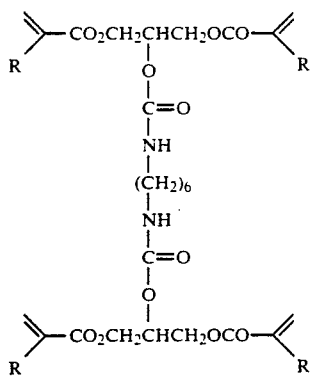

wherein R is H or CH₃, and

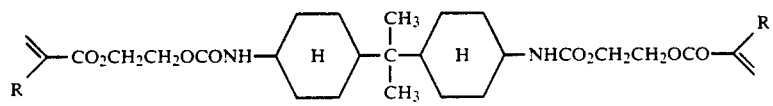

wherein R is H or CH₃, and

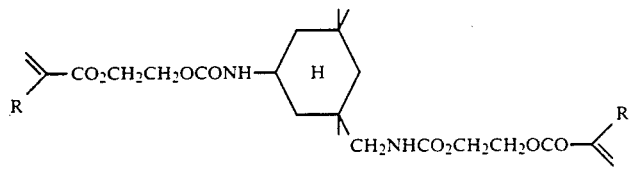

wherein R is H or CH₃.

Among these polyfunctional (meth)acrylate monomers. preferred are the monomers of formula (VI) and the urethane bond-containing monomers. Most preferred monomers are those of the following formulae:

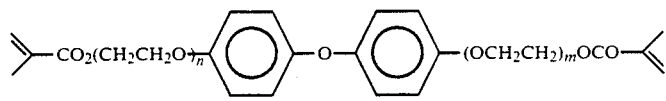

wherein m + n = 2 to 10, and

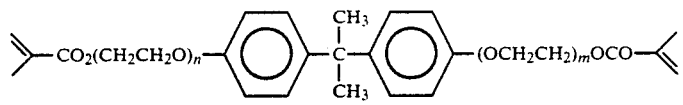

wherein m+n=2 to 10.

In the curable adhesive composition according to the present invention, the acrylate or methacrylate monomer containing an acidic group and at least one acryloyloxyl or methacryloyloxyl group in its moecule (R) which constitutes the curable composition (ii) includes (R1) aromatic polycarboxylic acids having at least one acryloyloxyl or methacryloyloxyl group per molecule or anhydrides thereof and (R2) partial esters of phosphoric or sulfonic acid having at least one acryloyloxyl or methacryloyloxyl group per molecule, such as monoesters and diesters of phosphoric acid, mixtures thereof, and monoesters of sulfonic acid. Examples of the aromatic polycarboxylic acid having at least one acryloyloxyl or methacryloyloxyl group per molecule (R1) are (meth)acryloyloxyl-containing aromatic polycarboxylic acids or anhydrides of the structure wherein an alkane polyol has at least two hydroxyl group per molecule and may contain an oxygen atom, at least one of its hydroxyl groups forms an ester with (meth)acrylic acid and at least one of its hydroxyl groups forms an ester with one carboxyl group of an aromatic polycarboxylic acid containing at least three carboxyl groups. The preferred aromatic polycarboxylic acids containing at least three carboxyl groups are aromatic polycarboxylic acids in which at least two of the carboxyl groups are attached to the adjoining carbon atom on the aromatic nucleus. Examples of the aromatic polycarboxylic acids are hemimellitic acid, trimellitic acid, prehnitic acid, mellophanic acid, and pyromellitic acid.

The (meth)acryloyloxyl-containing aromatic polycarboxylic acids or anhydrides thereof include 4(meth)acryloyloxymethoxycarbonylphthalic acid or an anhydride thereof, 4-(meth)acryloyloxyethoxycarbonylphthalic acid or an anhydride thereof, 4(meth)acryloyloxybutoxycarbonylphthalic acid or an anhydride thereof,

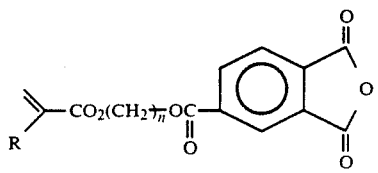

wherein R is H or CH₃, and n is an integer of from 6 to 12,

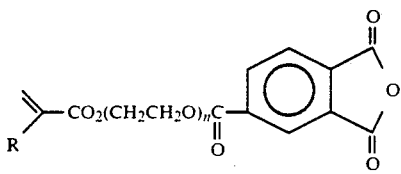

wherein R is H or CH₃, and n is an integer of from 2 to 50,

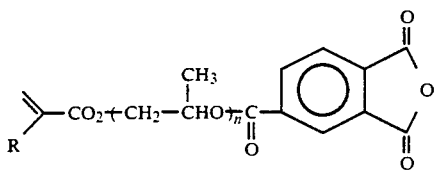

wherein R is H or CH₃, and n is an integer of from 1 to 50, 4-(2-hydroxy-3-acryloyloxypropoxycarbonyl)phthalic acid, 4-(2-hydroxy-3-methacryloyloxypropoxycarbonyl)phthalic acid or an acid anhydride thereof, 2,3-bis(3,4-dicarboxybenzoyloxy)propylacrylate, 2,3bis(3,4-dicarboxybenzoyloxy)propylmethacrylate or an acid anhydride thereof, and 2-(3,4-dicarboxybenzoyloxy)-1,3-diacryloyloxypropane, 2(3,4-dicarboxybenzoyloxy)-1,3-dimethacryloyloxypropane or an acid anhydride thereof.

The partial esters of phosphoric or sulfonic acid having at least one (meth)acryloyloxyl group per molecule (R2) include monoesters and diesters of phosphoric acid, mixtures thereof, and monoesters of sulfonic acid, for example, 2-acryloyloxyethylphenyl acid phosphate, 2methacryloyloxyethylphenyl acid phosphate, bis(2acryloyloxyethyl) acid phosphate, bis(2-methacryloyloxyethyl) acid phosphate, bis(3-acryloxypropyl) acid phosphate, bis(3-methacryloxypropyl) acid phosphate, 2- o acryloyloxyethylphenyl phosphonate, 2-methacryloyloxyethylphenyl phosphonate,

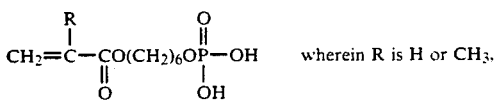 wherein R is H or CH₃,

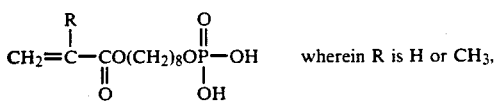 wherein R is H or CH₃,

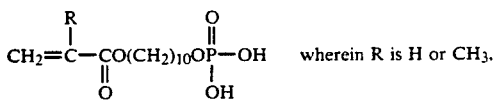 wherein R is H or CH₃,

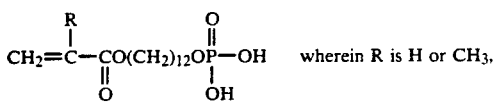 wherein R is H or CH₃,

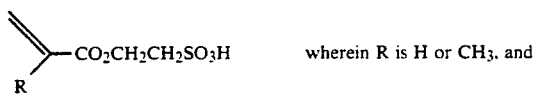 wherein R is H or CH₃, and

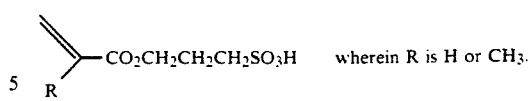 wherein R is H or CH₃.

Among these acrylate or methacrylate monomers containing an acidic group and at least one acryloyloxyl or methacryloyloxyl group in its molecule (R), preferred are aromatic polycarboxylic acids having at least one (meth)acryloyloxyl group per molecule or anhydrides thereof (R1). More preferred are 4-(meth)acryloyloxyethoxycarbonylphthalic acid and its acid anhydride. Most preferably, 4-(meth)acryloyloxyethoxycarbonylphthalic acid anhydride is used because of improved fitness or amenability to dentin.

The curable composition (ii) of the curable adhesive composition of the present invention further comprises (S) a trialkylboron or its oxide. This oxide also includes a partial oxide of trialkylboron. Examples of the trialkylboron include triethylboron, tripropylboron, triisopropylboron, tri-n-butylboron, tri-n-amylboron, triisoamylboron, tri-sec-amylboron, and oxides of these trialkylborons in which the trialkylborons are partially oxidized. Preferably, tri-n-butylboron and its partial oxides are used.

In the curable composition (ii) of the curable adhesive composition according to the present invention, the proportion of the monofunctional (meth)acrylate monomer (P) and the polyfunctional (meth)acrylate monomer (Q) blended therein is not particularly limited. Better results are obtained when the curable composition (ii) generally contains 5 to 95% by weight of the monofunctional (meth)acrylate monomer (P) and 95 to 5% by weight of the polyfunctional (meth)acrylate monomer (Q), preferably 10 to 95% by weight of the monofunctional (meth)acrylate monomer (P) and 90 to 5% by weight of the polyfunctional (meth)acrylate monomer (Q), and most preferably 25 to 90% by weight of the monofunctional (meth)acrylate monomer (P) and 75 to 10% by weight of the polyfunctional (meth)acrylate monomer (Q), based on the total weight of monomers (P) and (Q), because adhesiveness and fitness to dentin are improved, particularly adhesiveness and fitness to dentin etched with a mild acid such as EDTA as well as to non-etched dentin.

In the curable composition (ii) of the curable adhesive composition according to the present invention, the proportion of the acidic group-containing (meth)acrylate monomer (R) blended therein generally ranges from 1 to 50 parts by weight, preferably from 3 to 30 partsby weight, most preferably from 5 to 15 parts by weight per 100 parts by weight of the total of the monofunctional (meth)acrylate monomer (P) and the polyfunctional (meth)acrylate monomer (Q) blended therein.

In the curable composition (ii) of the curable adhesive composition according to the present invention, the proportion of the trialkylboron or its oxide (S) blended therein generally ranges from 2 to 100 parts by weight, preferably from 5 to 70 parts by weight, most preferably from 5 to 50 parts by weight per 100 parts by weight of the total of the monofunctional (meth)acrylate monomer (P), the polyfunctional (meth)acrylate monomer (Q), and the acidic group-containing (meth)acrylate monomer (R) blended therein. Since the trialkylboron or its oxide (S) starts polymerization reaction with the (meth)acrylate monomers (P), (Q), and (R) within several seconds to several ten minutes after their mixing, the trialkylboron (S) is kept separate from the (meth)acrylate monomers (P), (Q), and (R) and mixed with the latter monomers immediately before use.

The curable composition (ii) of the curable adhesive composition according to the present invention may contain any desired additives in addition to the above-mentioned essential components, for example, powder inorganic fillers, organic polymers, polymerization retarders, and pigments. Examples of the powder inorganic fillers include kaolin, talc, clay, calcium carbonate, silica, silica-alumina, alumina, titanium oxide, calcium phosphate, ground glass, and ground quartz. Examples of the organic polymers include wax, ethylene-vinyl acetate copolymers, and polymethylacrylate, polymethylmethacrylate, and copolymers thereof. These fillers or additives may be blended in any desired proportion.

The present invention also provides a method for applying a curable adhesive composition as defined above to a dental area, comprising dissolving the radical polymerizable acrylate or methacrylate monomer in a solvent to form solution (i), applying solution (i) to the dental area, removing the solvent, component (S) to form the composition (ii), applying the composition (ii) to the coated area immediately after mixing, and thereafter curing the resulting coating.

The curable adhesive composition of the present invention may be applied to a tooth, particularly a tooth cavity by applying the solution of a radical polymerizable acrylate or methacrylate monomer (i) to the surface of the tooth cavity, blowing air to the coated area to volatilize off the solvent, applying the curable composition (ii), and filling the cavity with a composite resin, and allowing the composition to cure.

The curable adhesive composition of the present invention has improved low-temperature curability at approximately room temperature and water resistant adherence, and exhibits excellent adhesiveness and fitness to tooth substance including enamel and dentin, particularly dentin, and gives no stimulation to dental pulp. Therefore, the composition can be used as a bonding agent not only for dental composite resins and rigid resins, but also for various composite resins used in precision working other than dental applications. Most preferably, the composition is used as a bonding agent for dental composite resins, especially as a bonding agent applied to dentin.

EXAMPLES

Examples of the present invention are presented below by way of illustration and not by way of limitation. Evaluation of the curable adhesive composition of the present invention is described below together with examples of preparing the composite filler and composite resin used in Examples and Comparative Examples. The abbreviations used herein have the following meanings.

MMA: methyl methacrylate,
HMA: n-hexyl methacrylate,
HEMA: 2-hydroxyethyl methacrylate,
HPMA: 2-hydroxypropyl methacrylate,
DPEMA:

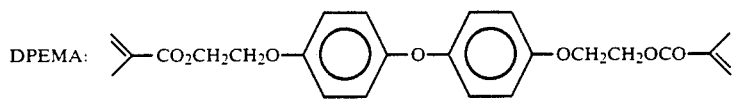

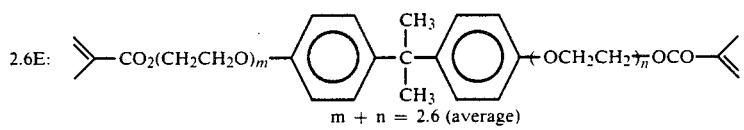

m + n = 2.6 (average)

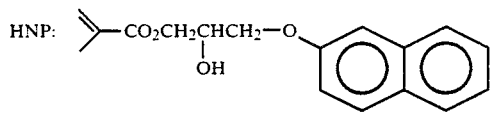

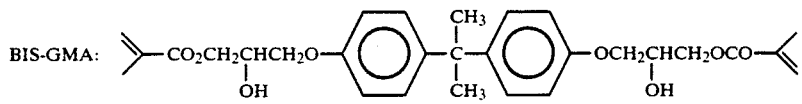

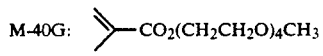

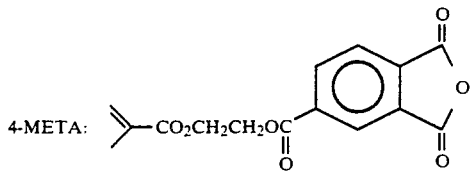

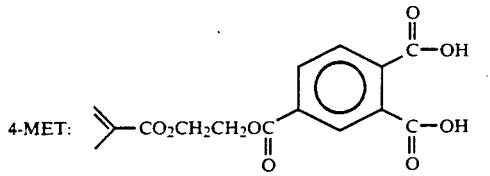

TBB-O: oxide of tri-n-butylboron

1. Evaluation of adhesiveness

The enamel or dentin surface of a bovine anterior tooth on its labial face was fully polished with every paper to #600 to smoothen the surface. The enamel was etched for 30 seconds with an aqueous solution of 65% phosphoric acid. The dentin was etched for 60 seconds with an aqueous solution of 0.3M EDTA-2Na and 0.2M EDTA-Fe-na at pH 7.4. After thorough rinsing, the etched surface was dried by air blowing. A piece of adhesive tape of about 13 mm by 13 mm having a circular opening of 5 mm in diameter was attached to the etched surface. The hydrophilic group-containing methacrylate solution described in Examples or Comparative Examples was applied to the surface in the opening and lightly air blown after 30 seconds. The curable composition described in Examples or Comparative Examples was applied to the once-coated surface in the opening, and lightly air blown after about 10 seconds. A cylindrical mold of polytetrafluoroethylene having a diameter of 5 mm and a height of 2 mm was mated with the circular opening in the adhesive tape and filled with the photo-polymerizable composite resin described later. The composite resin filling was covered on the surface with a cellophane sheet, and exposed for 30 seconds to visible light from a visible light source, Translux (manufactured by Kulzer) to cure the composite resin. An acryl resin bar was bonded to the surface of the cured composite resin with an adhesive, Super Bond C&B (manufactured by Sun Medical K.K.) to form a bond test specimen. The specimen was allowed to stand for 30 minutes at room temperature, immersed for 24 hours in water at a temperature of 37° C., allowed to stand for 10 minutes in air at a temperature of 23° C., and then subjected to a tensile test at a temperature of 23° C. and a pulling rate of 2 mm/min to measure a bonding force. The test used ten samples and the result is an average of ten measurements. After the bond test, the rupture surface exhibited bovine tooth rupture, cohesive rupture of the composite resin, or interfacial rupture between the composite resin and the dentin.

2. Evaluation of fitness to dentin cavity

The dentin surface of a bovine anterior tooth on its labial face was fully polished with emery paper to #600. A cylindrical cavity having a diameter of 3 mm and a depth of 1.5 mm was bored in the surface with water pouring. The cavity was etched for 60 seconds with an aqueous solution of 0.3M EDTA-2Na and 0.2M EDTA-Fe-Na at pH 7.4, thoroughly rinsed with water, and air blown. The predetermined hydrophilic group-containing methacrylate solution was applied to the cavity wall and lightly air blown after 30 seconds. Thereafter, the predetermined curable composition was applied to the cavity wall and lightly air blown after about 10 seconds. The cavity was then filled with the photo-polymerizable composite resin described later. A cellophane sheet was placed on the surface of the composite resin filling and lightly pressed. The filling was then exposed for 30 seconds to visible light from a visible light source, Translux (manufactured by Kulzer) to cure the composite resin. The resulting sample was immersed in water for 10 minutes, fully polished on the surface with #1500 emery paper under passing water, and observed under an optical microscope (X1,000) to determine the gap between the dentin cavity wall and the cured resin. The maximum gap divided by the diameter was expressed in percentage. The test used ten samples and the result is an average of ten measurements.

3. Preparation of photo-polymerizable composite resin

A composition was prepared by milling 7.5 grams of triethylene glycol dimethacrylate, 7.5 grams of 1,3-bis-(methacryloxyethoxy) benzene, 15 grams of an adduct of 1 mol of 2,2,4-trimethylhexamethylenediamine diisocyanate and 2 mol of 2-hydroxyethyl methacrylate, 40 grams of a composite filler synthesized by the following method, 30 grams of finely divided silica (RM-50, Nihon Aerosil K.K.), and 4 mg of hydroquinone monomethyl ether in a two roll mill at 35° C. A photo-curable composite resin was prepared by combining 10 grams of the composition with 45 mg of camphorquinone and 45 mg of 4-diethylaminobenzoic acid and fully admixing the mixture with a spatula.

4. Preparation of composite filler

A solution of 0.1 gram benzoyl peroxide in 10 grams of trimethylolpropane trimethacrylate was placed in a mortar. Finely divided silica (Aerosil R972, Nihon Aerosil K.K., average particle size of 16 mμ) was added to the solution in increments while mixing. As silica was added, the viscosity of the mixture gradually increased. When the mixture became somewhat crumby, it was transferred to a small-size rubber roll mill. Finely divided silica was further added in increments until a total amount of 9.5 grams was reached. The resulting paste was removed from the mill and heat cured for 10 minutes in a press at a mold temperature of 110° C. under a pressure of 150 to 200 kg/cm2 The cured product was ground in a ball mill so as to pass a 230 mesh screen, obtaining 18.0 grams of a composite filler. The filler had an average particle size of 11 μm.

EXAMPLE 1

The procedures for the application of solution or composition are the same as previously described in Evaluation of adhesiveness and Evaluation of fitness to dentin cavity.

A hydroxyl-containing methacrylate solution (i) was prepared by dissolving 3.5 grams of 2-hydroxyethyl methacrylate (HEMA) in 6.5 grams of distilled water. The hydroxyl-containing methacrylate solution (i) was applied to the dentin surface.

Separately, a monomer liquid for a curable composition (ii) was prepared by mixing 8.0 grams of methyl methacrylate (MMA), 1.0 gram of DPEMA, 1.0 gam of 4-META, 0.1 gram of polymethyl methacrylate(PMMA), and 2 mg of hydroquinone monomethyl ether at room temperature. The curable composition (ii) was prepared by mixing 2 parts by weight of the monomer liquid with 1 part by weight of a partial oxide of tri-n-butylboron (TBB-O, Sun Medical K.K.). The composition was applied on the solution-coated dentin surface with a small brush within 1 minute after mixing.

Specimens for the bond and fitness tests were then prepared. The results are shown in Table 1.

EXAMPLES 2-9 AND COMPARATIVE EXAMPLES 1-3

Specimens for the bond and fitness tests were prepared by following Example 1 except that the curable adhesive composition used in Example 1 was replaced by other curable adhesive compositions. These compositions were prepared by blending the monomers and PMMA reported in Table 1 in the amounts reported in Table 1. The results are shown in Table 1.

TABLE 1

| | Example 1 | Example 2 | Example 3 | Example 4 | Example 5 | Example 6 | Example 7 |
|---|---|---|---|---|---|---|---|
| Curable adhesive composition | | | | | | | |
| (i) solution | | | | | | | |
| Radical polymerizable monomer | HEMA | HEMA | HPMA | HEMA | HEMA | HEMA | HNP |
| Solvent | $H_2O$ | $H_2O$ | EtOH | $H_2O$ | $H_2O$ | $H_2O$ | Acetone |
| Monomer concentration, wt % | 35 | 35 | 30 | 35 | 15 | 35 | 20 |
| (ii) composition | | | | | | | |
| Monofunctional methacrylate monomer (P) type | MMA | MMA | MMA/HMA | MMA/HEMA | HMA | MMA/HEMA | MMA/HEMA |
| amount, weight ratio | — | — | 90/10 | 85/15 | — | 85/15 | 85/15 |
| Polyfunctional methacrylate monomer (Q) type | DPEMA | 2.6 E | 2.6 E | 2.6 E | 2.6 E | 2.6 E | 2.6 E |
| amount, Q/(P + Q) wt % | 11 | 11 | 40 | 50 | 50 | 50 | 50 |
| Acidic group-containing methacrylate monomer (R) type | 4-META | 4-META | 4-META | 4-META | 4-META | 4-MET | 4-META |
| amount, R/(P + Q) wt % | 11 | 11 | 11 | 11 | 11 | 6 | 11 |
| Partial oxide of trialkylboron (S) type | TBB · O | TBB · O | TBB · O | TBB · O | TBB · O | TBB · O | TBB · O |
| amount, S/(P + Q + R) wt % | 33 | 33 | 25 | 33 | 25 | 25 | 33 |
| PMMA, wt % based on monomers | 1 | 1 | 0 | 0 | 0 | 0 | 0 |
| Adhesiveness | | | | | | | |
| Enamel, after water immersion @ 37° C., 1 day, kg/cm² | 190 | 195 | 205 | 206 | 201 | 193 | 200 |
| Dentin, after water immersion @ 37° C., 1 day, kg/cm² | 126 | 130 | 131 | 133 | 127 | 125 | 125 |
| Fitness to dentin cavity | | | | | | | |
| Maximum polymerization shrinkage gap, % | 0 | 0 | 0 | 0 | 0 | 0 | 0 |

| | Example 8 | Example 9 | Comparative Example 1 | Comparative Example 2 | Comparative Example 3 |
|---|---|---|---|---|---|
| Curable adhesive composition | | | | | |
| (i) solution | | | | | |
| Radical polymerizable monomer | BISGMA | M-40G | — | HEMA | HEMA |
| Solvent | EtOH | $H_2O$ | — | $H_2O$ | $H_2O$ |
| Monomer concentration, wt % | 20 | 20 | 0 | 35 | 35 |
| (ii) composition | | | | | |
| Monofunctional methacrylate monomer (P) type | MMA/HEMA | MMA/HEMA | MMA | MMA | MMA |
| amount, weight ratio | 85/15 | 85/15 | — | — | — |
| Polyfunctional methacrylate monomer (Q) type | 2.6 E | 2.6 E | DPEMA | — | 2.6 E |
| amount, Q/(P + Q) wt % | 50 | 50 | 11 | 0 | 11 |
| Acidic group-containing methacrylate monomer (R) type | 4-META | 4-META | 4-META | 4-META | — |
| amount, R/(P + Q) wt % | 11 | 11 | 11 | 11 | 0 |
| Partial oxide of trialkylboron (S) type | TBB · O | TBB · O | TBB · O | TBB ; O | TBB · O |
| amount, S/(P + Q + R) wt % | 33 | 33 | 33 | 33 | 33 |
| PMMA, wt % based on monomers | 0 | 0 | 1 | 1 | 1 |
| Adhesiveness | | | | | |
| Enamel, after water immersion | 195 | 192 | 190 | 135 | 133 |

TABLE 1-continued

| | | | | | |
|---|---|---|---|---|---|
| @ 37° C., 1 day, kg/cm² Dentin, after water immersion | 125 | 128 | 110 | 65 | 25 |
| @ 37° C., 1 day, kg/cm² Fitness to dentin cavity | | | | | |
| Maximum polymerization shrinkage gap, % | 0 | 0 | 0.08 | 0.12 | 0.20 |

We claim:

1. A two part curable adhesive composition comprising as a first part (i) a solution comprising a radical polymerizabel acrylate or methacrylate monomer having in its molecule at least one group selected from the class consisting of hydroxyalkyl, hydroxyalkylene, amide, oxyalkylene and polyoxyalkylene groups, and a solvent for said radical polymerizable acrylate or methacrylate monomer; and as a second part (ii) a curable composition comprising
 (P) a monofunctional acrylate or methacrylate monomer,
 (Q) a plyfunctional acrylate or methacrylate monomer,
 (R) an acrylate or methacrylate monomer containing an acidic group and at least one acryloyloxyl or methacryloyloxyl group in its molecule, and
 (S) a trialkylboron or an oxide thereof;
wherein said component (S) is maintained separate from said components (P), (Q) and (R) until immediately before use.

2. The composition of claim 1 wherein the curable composition (ii) comprises 5 to 95% by weight of (P) and 95 to 5% by weight of (Q) based on the total weight of (P) and (Q), 1 to 50 parts by weight of (R) per 100 parts by weight of the total of (P) and (Q), and 2 to 100 by weight of (S) per 100 parts by weight of the total of (P), (Q) and (R).

3. A method for applying, to a dental area, two-part curable adhesive composition comprising as a first part (i) a solution comprising a radical polymerizable acrylate or methacrylate monomer having in its molecule at least one group selected from the class consisting of hydroxyalkyl, hydroxyalkylene, amide, oxyalkylene and polyoxyalkylene groups, and a solvent for said radical polymerizable acrylate or methacrylate monomer; and as a second part (ii) a curable composition comprising (P) a monofunctional acrylate or methacrylate monomer, (Q) a polyfunctional acrylate or methacrylate monomer, (R) an acrylate or methacrylate monomer containing an acidic group and at least one acryloyloxyl or methacryloyloxyl group in its molecule and (S) a trialkylboron or an oxide thereof; wherein said component (S) is maintained separate from said components (P), (Q) and (R) until immediately before use; said method comprising:

dissolving said radical polymerizable acrylate or methacrylate monomer in said solvent to form said solution (i);

applying said solution (i) to a dental area;

removing said solvent from said applied solution to form a coated area;

mixing said components (P), (Q) and (R) with said component (S) to form said composition (ii);

applying said composition (ii) to said coated area immediately after mixing to form a coating; and curing said coating.

* * * * *